US012018760B2

(12) United States Patent
Stirnweiss et al.

(10) Patent No.: US 12,018,760 B2
(45) Date of Patent: Jun. 25, 2024

(54) VALVE SLIDE FOR A VALVE UNIT USED AS AN INSUFFLATION AND PURGING VALVE, VALVE UNIT HAVING A CORRESPONDING VALVE SLIDE, AND METHOD FOR PRODUCING A VALVE SLIDE

(71) Applicant: FUJIFILM MEDWORK GMBH, Höchstadt/Aisch (DE)

(72) Inventors: Matthias Stirnweiss, Lonnerstadt (DE); Gerald Fischer, Höchstadt/Aisch (DE)

(73) Assignee: FUJIFILM MEDWORK GMBH, Höchstadt/Aisch (DE)

( * ) Notice: Subject to any disclaimer, the term of this patent is extended or adjusted under 35 U.S.C. 154(b) by 953 days.

(21) Appl. No.: 16/969,685

(22) PCT Filed: Jan. 23, 2019

(86) PCT No.: PCT/DE2019/100071
§ 371 (c)(1),
(2) Date: Aug. 13, 2020

(87) PCT Pub. No.: WO2019/158149
PCT Pub. Date: Aug. 22, 2019

(65) Prior Publication Data
US 2020/0400241 A1    Dec. 24, 2020

(30) Foreign Application Priority Data
Feb. 14, 2018 (DE) .................. 10 2018 103 355.9

(51) Int. Cl.
*A61B 1/00* (2006.01)
*F16K 11/07* (2006.01)

(52) U.S. Cl.
CPC ...... *F16K 11/0712* (2013.01); *A61B 1/00068* (2013.01); *A61B 1/0011* (2013.01); *A61B 1/00119* (2013.01); *F16K 11/0716* (2013.01)

(58) Field of Classification Search
CPC .................. A61B 1/00068; A61B 1/00119
See application file for complete search history.

(56) References Cited

U.S. PATENT DOCUMENTS

| 4,311,134 A | * | 1/1982 | Mitsui | ............... A61B 1/00068 |
| | | | | 600/157 |
| 4,748,970 A | | 6/1988 | Nakajima | |

(Continued)

FOREIGN PATENT DOCUMENTS

| EP | 3073889 A1 | 10/2016 |
| EP | 3108799 A1 | 12/2016 |

(Continued)

OTHER PUBLICATIONS

International Search Report Dated May 27, 2019, PCT/DE2019/100071, 2 Pages.

*Primary Examiner* — Aaron B Fairchild
(74) *Attorney, Agent, or Firm* — LUCAS & MERCANTI, LLP; Klaus P. Stoffel (57) ABSTRACT

A valve slide for a valve unit used as an insufflation and purging valve, which valve slide has a proximal actuating section, which is led through a holder and has an actuating knob. The actuating knob is supported on the holder via a compression spring on the one hand, and wherein an annular projection of the valve slide interacts with the holder as a stop acting in the axial direction on the other hand. At the distal control section of the valve slide, sealing rings are provided, which project radially beyond the valve slide, an outer lateral surface of the distal control section, apart from radial guide sections possibly provided on the latter and the projection, is formed with a smooth wall, and the sealing rings are connected integrally to the smooth-walled outer lateral surface.

5 Claims, 5 Drawing Sheets

(56) References Cited

U.S. PATENT DOCUMENTS

| | | |
|---|---|---|
| 9,408,523 B2 | 8/2016 | Grudo |
| 2008/0027283 A1* | 1/2008 | Matsui ............ A61B 1/041 |
| | | 600/129 |
| 2015/0011831 A1* | 1/2015 | Ouchi ............ A61B 1/05 |
| | | 600/159 |
| 2015/0257634 A1* | 9/2015 | Nakade ............ A61B 1/005 |
| | | 600/159 |
| 2016/0309987 A1 | 10/2016 | Grudo |
| 2017/0143194 A1 | 5/2017 | Wolfe |

FOREIGN PATENT DOCUMENTS

| | | |
|---|---|---|
| EP | 3073889 B1 | 4/2019 |
| JP | H09201326 A | 8/1997 |
| JP | 2005261512 A | 9/2005 |
| JP | 2013545555 A | 12/2013 |
| JP | 2016539695 A | 12/2016 |
| WO | 2012075131 A1 | 6/2012 |
| WO | 2017091459 A9 | 6/2017 |

\* cited by examiner

VALVE SLIDE FOR A VALVE UNIT USED AS AN INSUFFLATION AND PURGING VALVE, VALVE UNIT HAVING A CORRESPONDING VALVE SLIDE, AND METHOD FOR PRODUCING A VALVE SLIDE

The present application is a 371 of International application PCT/DE2019/100071, filed Jan. 23, 2019, which claims priority of DE 10 2018 103 355.9 filed Feb. 14, 2018, the priority of these applications is hereby claimed and the applications are incorporated herein by reference.

BACKGROUND OF THE INVENTION

Field of the Invention

The invention relates to a valve slide for a valve unit, serving as an insufflation and purging valve, of a medical endoscope, which valve slide can be inserted by way of a distal control section into a receiving bore which is configured at least indirectly in a manual actuation part of the endoscope and is connected to air inlet channels and air outlet channels and to purging liquid inflow channels and purging liquid outlet channels, the valve slide having a proximal actuating section which is guided through a retaining ring and is provided with an actuating button, the actuating button being supported firstly on the retaining ring via a compression spring, and secondly an annular projection of the valve slide interacting as a stop which acts in the axial direction with the retaining ring, and sealing rings being provided on the distal control section of the valve slide, which sealing rings project radially beyond the valve slide and are provided to seal at least one control space of the valve unit in a manner which slides on an inner circumferential face of the receiving bore.

Furthermore, the invention also relates to a valve unit of a medical endoscope, which valve unit serves as an insufflation valve and a purging valve with a common valve slide which is arranged by way of a distal control section in a receiving bore of a valve housing such that it can be displaced, an air inlet channel which is connected to a compressed air source and a purging liquid inflow channel which is connected to a liquid supply opening into the receiving bore, and an air outlet channel and a purging liquid outlet channel emanating from said receiving bore, which channels lead to a distal end of the endoscope, the valve slide being provided with a proximal actuating section which projects axially beyond a retaining ring which encloses the valve slide, which actuating section is connected at its end to an actuating button, the actuating button being supported firstly on the retaining ring via a compression spring, and secondly an annular projection of the valve slide interacting as a stop which acts in the axial direction with the retaining ring, sealing rings being provided on the distal control section of the valve slide, which sealing rings project radially beyond the valve slide and are guided in a sliding manner on an inner circumferential face of the receiving bore, in order to seal control spaces of the valve unit with respect to one another.

Finally, the invention also relates to a method for producing a valve slide for a valve unit, consisting of an insufflation valve and a purging valve, of a medical endoscope, which valve slide has a proximal actuating section, sealing rings being provided on a distal control section of the valve slide.

PRIOR ART

Endoscopes which are used in flexible endoscopy are provided at their proximal manual actuation part with a valve unit which consists of an insufflation valve and a purging valve and as a rule consists of a valve slide which is arranged displaceably in a receiving bore of the manual actuation part. As an alternative to this, the valve unit can also have a valve housing, by way of which it is inserted into the receiving bore of the manual actuation part.

In the case of the insufflation function, the entry of a gaseous medium, for example air or $CO_2$, into a cavity in the body of the patient, in which cavity an endoscopic procedure is to be performed, is controlled, the gaseous medium which flows into said cavity ensuring that the volume of the latter increases. The gaseous medium is fed to the valve unit from a gas cylinder or a compressed air system. An outlet channel for the gaseous medium, which outlet channel is controlled by means of the valve slide, is routed as far as a distal end of the endoscope. If air is used as gaseous pressure medium, the valve slide is usually configured in such a way that, when no insufflation operation is being carried out, the air exits from an actuating button via a longitudinal bore which on said actuating button.

Furthermore, the valve slide has a section which is a constituent part of a purging valve. A purging liquid which is loaded with a pressure is fed from a storage vessel to the purging valve, the purging liquid likewise being conducted to the distal end of the endoscope via a purging liquid outlet channel in the open position of said purging valve. Here, the purging liquid which exits from the endoscope passes onto a surface of a window which is provided at the distal end of the endoscope and behind which a lens of the endoscope is situated, and cleans said lens.

A valve slide for a valve unit which consists of an insufflation valve and a purging valve, a valve unit with a corresponding valve slide, and a method for producing a valve slide of the generic type are known from WO 2012/075131 A1. Here, the valve slide which is called a main shank and is to be arranged longitudinally displaceably in a receiving bore has a multiplicity of ribs and grooves which run on it in the circumferential direction and are configured monolithically with the main shank. Seals are arranged in the grooves, which seals are to be produced and attached in the grooves by virtue of the fact that that region of the valve slide which is provided with the respective groove is over-molded with the seal material.

This achieves a situation where the seal is received by the groove, whereas a section of the seal, which section projects radially beyond the groove, is guided in a sliding manner on an inner circumferential face of the receiving bore and seals pressure spaces with respect to one another within the valve unit. A proximal part region of the valve slide is provided with a centrally running longitudinal bore, from which a transverse bore emanates distally and which opens at the proximal end of the valve slide. Over the entire length, the valve slide is provided with a multiplicity of diameter steps, in order to form the grooves, ribs and piston-like projections. The valve slide is inserted by way of a recessed proximal end section into a sleeve, the end section penetrating a membrane which is provided in the interior of the sleeve and being provided at its end-side end with an actuating button which likewise has a central bore.

The insufflation function of the valve unit is controlled by virtue of the fact that the central bore and therefore the longitudinal bore which runs in the valve slide are closed by way of a finger of the person operating the endoscope. As a result, the gaseous medium flows from an air inlet channel into an air outlet channel of the valve unit. If the finger is lifted up from the bore, the gaseous medium passes out of the valve unit via said bore. On its distal end section, the valve slide forms a control space with the receiving bore, via which control space a purging liquid inflow channel and a purging liquid outlet channel can be connected to one another.

Furthermore, U.S. Pat. No. 4,748,970 A and WO 2017091459 A9 have in each case disclosed a valve unit which consists of an insufflation valve and a purging valve and is substantially identical to the valve unit according to WO 2012/075131 A1 with regard to its construction and its function. Here, grooves and ribs are likewise configured monolithically with a main shank or valve slide. According to U.S. Pat. No. 4,748,970 A, a seal which is inserted into a groove of the main shank serves as a check valve between an air outlet channel and an air inlet channel. Otherwise, seals are clearly to be dispensed with, by the valve slide being guided in a cylinder in a sealing manner. According to WO 2017091459 A9, a plurality of seals and guide rings are inserted into grooves of the valve slide. Inter alia, a seal with two sealing lips is provided for the control of the purging liquid stream, which sealing lips are connected to one another via a cylindrical section.

SUMMARY OF THE INVENTION

It is an object of the present invention to provide a valve slide for a valve unit which consists of an insufflation valve and a purging valve, which valve slide can be produced inexpensively on a large scale using the injection molding method, and has advantages with regard to its functionality.

Accordingly, a valve slide for a valve unit, serving as an insufflation and purging valve, of a medical endoscope is to have a distal control section and is to be capable of being inserted into a receiving bore which is configured at least indirectly in a manual actuation part of an endoscope and is connected to air inlet channels and air outlet channels and to purging liquid inflow channels and purging liquid outlet channels. The valve slide has a proximal actuating section which is guided through a retaining ring and is provided with an actuating button, the actuating button being supported firstly on the retaining ring via a compression spring, and secondly an annular projection of the valve slide interacting as a stop which acts in the axial direction with said retaining ring.

Sealing rings are provided on the distal control section, projecting axially beyond the retaining ring, of the valve slide, which sealing rings project radially beyond the valve slide and are provided to seal control spaces of the valve unit with respect to one another in a manner which slides on an inner circumferential face of the receiving bore. As a consequence, the sealing rings which are preferably provided with sealing lips serve to seal the control spaces, to which pressure medium is fed, in order that the streams, guided as far as the distal end of the endoscope, of the gaseous medium which is required for an insufflation operation and of the liquid stream which is required for a purging operation can be controlled via the valve slide.

Here, according to the invention, an outer circumferential face of the distal control section is to be of smooth-walled configuration apart from radial guide sections which are possibly provided on said outer circumferential face, and the sealing rings are to be connected in an integrally joined manner to the smooth-walled outer circumferential face. Therefore, no means are provided on the outer circumferential face, by means of which means a positively locking connection is achieved between the valve slide and the sealing rings. The latter are fixed on the outer circumferential face exclusively via an integrally joined connection.

This results in considerable advantages in the case of the production of the valve slide. The smooth-walled surface is interrupted solely and exclusively by way of guide sections which project radially beyond the outer circumferential face and serve to guide the valve slide in a receiving bore. The control spaces are produced by way of the radial spacing between the outer circumferential face of the valve slide and an inner circumferential face of the receiving bore. There is of course also the possibility to provide the guide sections on the inner circumferential face, it then also being possible for a radial collar or projections to be dispensed with in the case of the smooth-walled distal control section of the valve slide.

Furthermore, a valve unit of a medical endoscope, which valve unit serves as an insufflation valve and a purging valve with a common valve slide, is to be arranged by way of a distal control section in a receiving bore of a housing such that it can be displaced. Here, an air inlet channel which is connected to a compressed air source and a purging liquid inflow channel which is connected to a liquid supply open into the receiving bore, and an air outlet channel and a purging liquid outlet channel emanate from said receiving bore, which channels lead to a distal end of the endoscope. The valve slide is provided with control sections and a proximal actuating section which projects axially beyond a retaining ring which encloses the valve slide, which actuating section is connected at its end to an actuating button.

Said actuating button is supported firstly on the retaining ring via a compression spring, and secondly an annular projection of the valve slide interacts as a stop which acts in the axial direction with said retaining ring. Sealing rings are provided on the distal control section of the valve slide, which sealing rings project radially beyond the valve slide and are guided in a sliding manner on an inner circumferential face of the receiving bore, in order to seal control spaces of the valve unit with respect to one another. Regions which are delimited in the axial direction by way of the sealing rings are called control sections, with the result that control spaces are delimited together with the receiving bore.

Here, an outer circumferential face of the distal control section is likewise to be of smooth-walled configuration, apart from radially projecting guide sections which are possibly provided on said outer circumferential face, the sealing means being connected in an integrally joined manner to the smooth-walled outer circumferential face. In this case, a valve slide which is configured according to the invention is a constituent part of a valve unit.

In contrast, according to WO 2012/075131 A1 and the further documents U.S. Pat. No. 4,748,970 A and WO 2017091459 A9, the sealing rings are arranged in each case in grooves of the main body which is provided for the valve slide, in order that they are held in their position on the main body by way of a positively locking connection. Since the respective main body has a centrally running longitudinal channel, a relatively great wall thickness is to be provided between the longitudinal channel and its outer circumferential face for a configuration of grooves of this type, which is difficult in the case of the small dimensions of the valve unit. Moreover, the valve units have to be sterilized before use in an endoscope, in order that the latter is free from germs. In comparison with a smooth surface, to which sealing rings are connected in an integrally joined manner, it is considerably more difficult to sterilize a complete valve slide which has grooves which receive sealing rings in a positively locking manner.

Moreover, according to the invention, the valve slide is to be configured as a prism-like hollow body with a circularly annular cross section, in which a longitudinal channel is provided for conducting the compressed air. The hollow body is to be produced from a thermoplastic using injection molding. Since no grooves are provided in the hollow body, the latter can overall have a small and virtually constant wall thickness.

It is provided in a further refinement of the invention that the hollow body is produced from acrylonitrile butadiene styrene, and the sealing rings are produced from a thermoplastic elastomer. In this way, the two components are produced from materials, the melting points of which lie close to one another. Therefore, an optimum integrally joined connection can be achieved in the case of molding on of the seals, in the case of which the hollow body has a surface temperature of from 60 to 100° C.

It is provided, furthermore, that the hollow body is of frustoconical configuration at least in the distal region of the control section of the valve slide. Said first frustoconical part section can be adjoined in the axial direction by a further frustoconical part section. The radial dimensions of the receiving bore of step-like configuration are adapted to said radial dimensions of the valve slide, that is to say a last control section in the distal direction has the smallest diameter.

Moreover, the guide sections are to be configured as runners which are distributed uniformly on the circumference of the hollow body and are formed by way of attachments which extend radially from the circumference. As a result, the valve slide can be displaced in the receiving bore with a low friction on account of the reduced guide area.

At least one transverse bore which communicates with the longitudinal channel is to be provided in the wall of the hollow body in a region which lies between two sealing rings. The compressed air is fed to the longitudinal bore via said transverse opening. Here, the air inlet channel is connected permanently to a control channel which opens on the end side of the actuating section. Said control channel lies in an end side of an actuating button which is fixed on the valve slide, and can be covered by way of the finger in order to control the compressed air stream for an insufflation.

It is provided, moreover, that a sealing ring which serves to control the compressed air stream and assumes a position between the air inlet channel and the air outlet channel in the two switching positions of the valve slide acts as a check valve and releases only a compressed air stream from the air inlet channel to the air outlet channel. This can be a grooved ring, the sealing lip of which lifts up in a pressure-dependent manner from the sealing region which is provided in the receiving bore.

In an axial section which is adjacent to its distal end and is connected to the purging liquid inflow channel, the receiving bore which receives the valve slide is to be widened radially with respect to a sealing region which adjoins it in the proximal direction. In the case of a manual axial displacement of the valve slide, the last sealing ring in the distal direction passes into said radially widened region of the receiving bore, with the result that the purging liquid inflow channel and the purging liquid outlet channel are connected to one another for a purging operation.

Furthermore, the object is also achieved in the case of a method for producing a valve slide for a valve unit, consisting of an insufflation valve and a purging valve, of a medical endoscope, which valve slide is of piston valve-like configuration and has a proximal actuating section; sealing rings are to be provided on a distal control section of the valve slide.

It is provided here that the valve slide which is configured as a prism-like hollow body with a circularly annular cross section is produced in a first working step in a first injection mold which receives a core and has an outer circumferential face of smooth-walled configuration, on which radial guide sections are provided, and that said prism-like hollow body is inserted in the state, in which it has not yet cooled, in a second working step into a second injection mold which has outer contours of the sealing rings, and the sealing rings are molded onto the smooth-walled outer circumferential face of the hollow body. The injection molds preferably consist of two mold halves with in each case two cavities, with the result that each of the method steps serves to produce two valve slides.

In a further refinement of said method, the melting points of the materials which are used for the hollow body and the sealing rings are to lie close to one another. The melting point is the temperature, at which a material changes from its solid into the liquid physical state. Accordingly, acrylonitrile butadiene styrene can be provided as material of the hollow body, and a thermoplastic elastomer can be provided as material of the sealing rings. The hollow body is to have a surface temperature of 60-100° in the case of molding on of the sealing rings.

The invention is not restricted to the specified combination of the features described. Moreover, this results in possibilities to combine individual features with one another, even in so far as they are apparent from the patent claims, the specifications of the advantages in respect of the patent claims, the following description of the exemplary embodiments or at least from the drawing. The reference of the patent claims to the drawing by way of the use of designations is not intended to restrict the scope of protection of the patent claims.

BRIEF DESCRIPTION OF THE DRAWING

For further explanation of the invention, reference is made to the figures, in which one exemplary embodiment of the invention is shown in a simplified manner and in which.

DETAILED DESCRIPTION OF THE INVENTION

Figure 1:
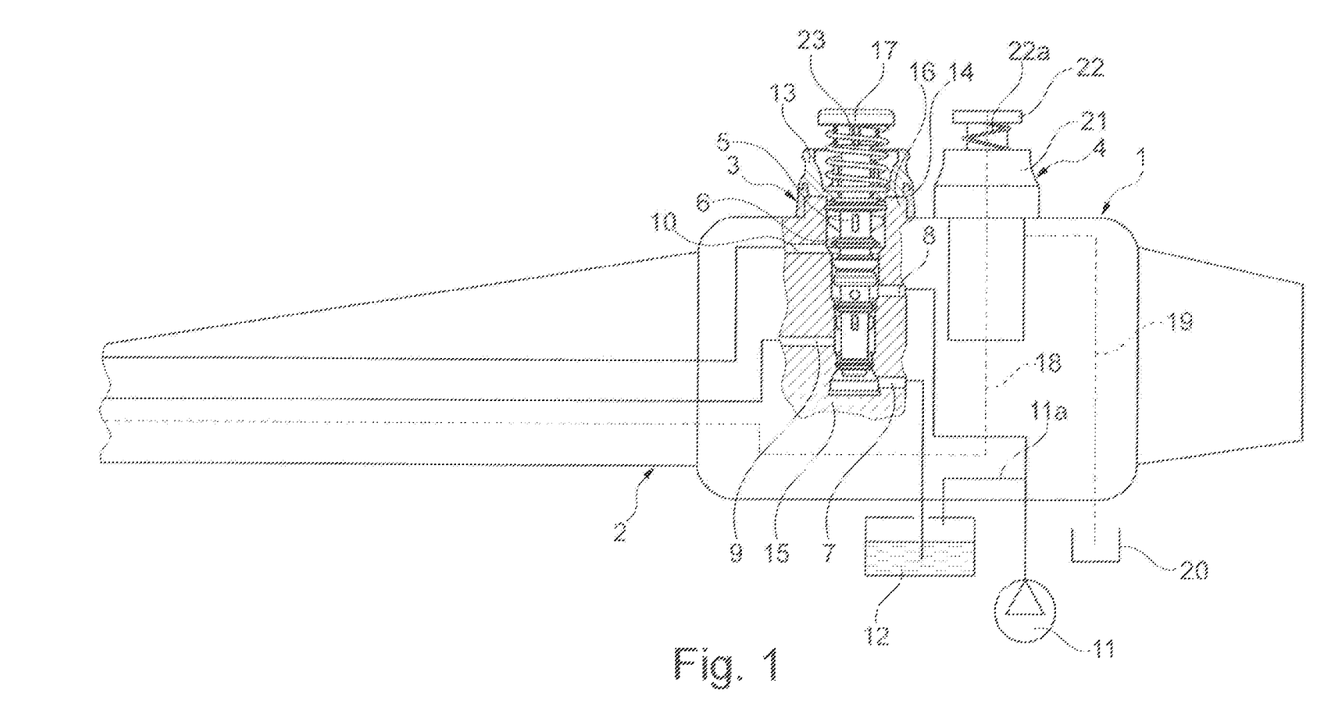
FIG. 1 shows a diagrammatic partial view of an endoscope with a valve unit which is arranged therein and is shown in longitudinal section.

In FIG. 1, 1 denotes a manual actuation part of an endoscope 2, in which a valve unit 3 which is configured according to the invention and serves as an insufflation valve and a purging valve is arranged. The endoscope 2 has an insertion tube which is not shown in greater detail and the distal end of which can be introduced into a gastrointestinal tract of a patient to be treated. Furthermore, the manual actuation part 1 which is arranged on the endoscope 2 in a proximal manner receives a drain valve 4.

The valve unit 3 has a valve slide 5 which is arranged in a receiving bore 6 of the manual actuation part 1 such that it can be displaced longitudinally. Here, a purging liquid inflow channel 7 and an air inlet channel 8 open into the receiving bore 6, whereas a purging liquid outlet channel 9 and an air outlet channel 10 emanate from the receiving bore 6, which channels run as far as the distal end (not shown in greater detail) of the endoscope 2. Instead of air, another gaseous medium, for example $CO_2$, can also be used for the insufflation.

The purging liquid inflow channel 7 and the air inlet channel 8 are preferably a constituent part of a supply line which emanates from the manual actuation part 1. By means of said supply line, the endoscope 2 is connected to a compressed air source 11 which firstly conveys compressed air into the air inlet channel 8 and secondly loads a purging liquid storage vessel 12 with pressure via a pressure line 11a, with the result that the purging liquid which is situated in said purging liquid storage vessel 12 is driven out into the purging liquid inflow channel 7.

Purging liquid which passes into the purging liquid outlet channel 9 in an open position of a section of the valve unit 3, which section serves as a purging valve, is conducted at the distal end of the endoscope onto a surface of a window which is not shown in greater detail and behind which a lens of the endoscope 1 is situated, with the result that said window is cleaned. The air which passes into the air outlet channel 10 and which, as an alternative, can also be another gaseous medium, such as $CO_2$, is guided via the distal end of the endoscope 2 into a cavity in the body of the patient, in order to increase the volume of said cavity within the context of an insufflation.

The valve slide 5 is guided by way of a proximal end section in a retaining ring 13, the latter being enclosed by an elastic sleeve 14 on an axial part section. A housing 15 of the manual actuation part 1 has a projecting collar 16 which is engaged around here by the sleeve 14. As can be gathered, furthermore, from the illustration, the valve slide receives an actuating button 17 at its proximal end. Said actuating button 17 supports itself and therefore the valve slide 5 on the retaining ring 13 via a compression spring 23. The further details of the configuration of the valve unit 3 are to be described in the following text on the basis of the further figures.

The abovementioned drain valve 4 is configured as a 2/2-way valve, and is connected via a drain channel 18 to the distal end of the endoscope 2, said drain valve 4 conducting, in its open state, liquid from the cavity of the body via a collecting channel 19 into a collecting reservoir 20. Here, the drain valve 4 likewise has a valve slide which can be displaced in a retaining ring 21, can be actuated by means of a pushbutton 22, and is supported on the retaining ring 21 in the axial direction via a compression spring 22a.

Figure 2:
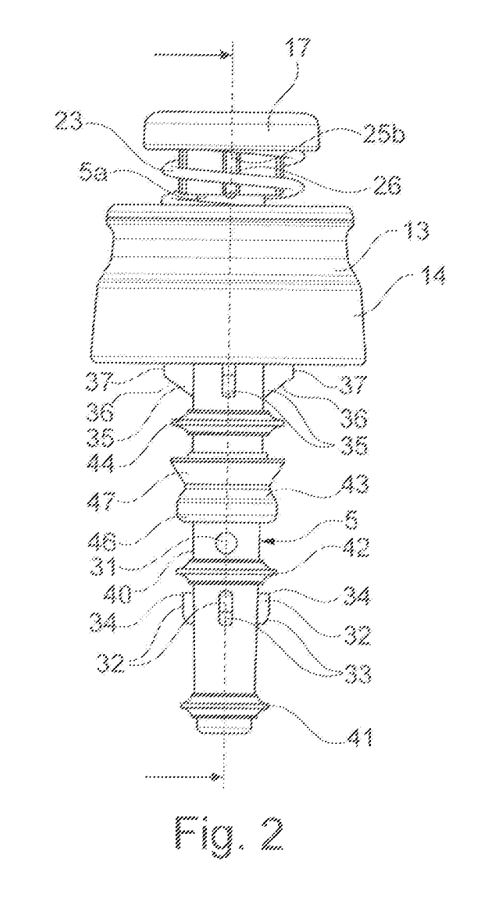
FIG. 2 shows a side view of a valve slide of the valve unit, which valve slide is arranged in a retaining ring.
Figure 3:
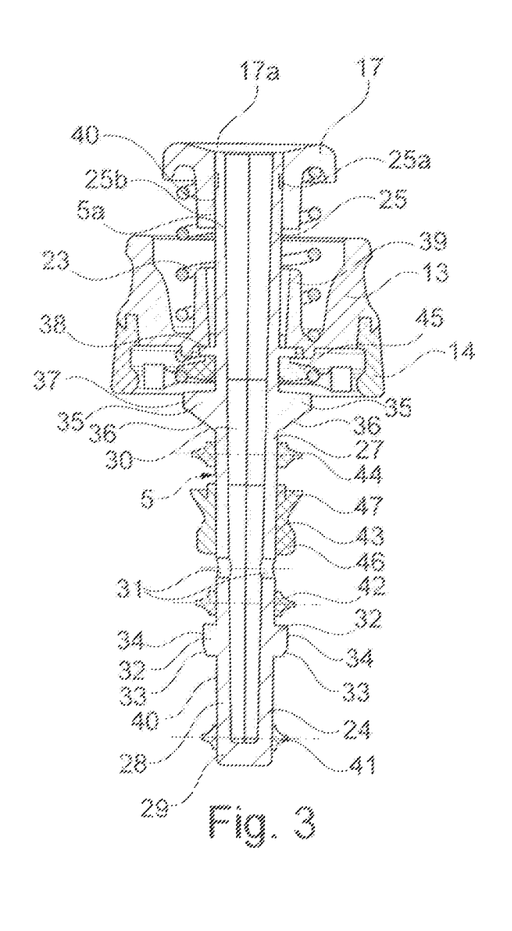
FIG. 3 shows a longitudinal section according to line III-III through the valve slide and the retaining ring in FIG. 2.

FIGS. 2 and 3 show the unit which consists of the valve slide 5 and the retaining ring 13 and is a constituent part of the valve unit 5 which is shown in FIG. 1. It is apparent here from FIG. 3, in particular, that the valve slide 5 consists of a prism-like hollow body 24 with a circularly annular cross section, the hollow body 24 comprising three part sections of different configuration, as viewed in the longitudinal direction. In a proximal part section, the hollow body 24 is of substantially cylindrical configuration, that is to say its outer wall 25 runs with a constant internal and external diameter, apart from an end-side groove 25a and longitudinally running ribs 25b. An outer circumferential face 40 of the hollow body 24 is of smooth-walled configuration.

This is adjoined by a middle region of the hollow body 24, in which middle region a second region, as a circumferential outer wall 27, differs from the cylindrical shape at a slight angle, as viewed in the longitudinal direction, that is to say is of frustoconical configuration. Finally, said second region is adjoined by a third region, in which a third outer wall 28 likewise runs in a frustoconical manner at a more pronounced inclination than the outer wall 27. The axial extents of the sections of different configuration with the correspondingly running outer walls 25, 27 and 28 are identified by way of lines which run transversely within a longitudinal channel 30.

At its distal end, the prism-like hollow body 24 is closed by way of an end-side wall 29. Overall, the longitudinal channel 30 is produced by way of the above-described hollow configuration of the hollow body 24 which forms the valve slide 5 and extends within the hollow body 24 axially from the wall 29 as far as its proximal end. Two transverse bores 31 emanate from said longitudinal channel 30, which transverse bores 31 are configured in the outer wall 28 of the third part section. Furthermore, said outer wall 28 is provided with first runners 32 which extend in each case radially from the outer wall 28 and are arranged offset circumferentially with respect to one another by in each case 90°. Each runner 32 has a bevel 33 and, otherwise, an end 34 which runs concentrically with respect to the outer wall 28.

Second runners 35 are provided on the outer wall 27 of the middle part section of the hollow body 24, which second runners 35 likewise extend radially from said middle part section and are offset circumferentially with respect to one another by 90°. Said second runners 35 also in each case have a bevel 36 and an end 37 which runs concentrically with respect to the outer wall 27. The span width which is measured via the ends of the diametrically running runners 32 and 35 is greater in the case of the second runners than in the case of the first runners 32. Otherwise, a radially projecting, annular projection 38 is configured on the outer wall 25 of the first part section, which projection 38 acts, as is apparent from FIG. 3, moreover, as an axial stop between the valve slide 5 and the retaining ring 13.

The valve slide 5 is guided by way of its proximal end 5a through a hub 39 of the retaining ring 13, the compression spring 23 which runs partially within the retaining ring 13 and encloses the hollow body 24 on an axial section being supported firstly on the retaining ring 13 and secondly on the actuating button 17. Here, the actuating button 17 is fixed on an outer circumferential face 40 of the hollow body 24, longitudinal slots 26 of the actuating button 17 engaging around the ribs 25b, and the longitudinal channel 30 opening on an end side 17a of trough-like configuration of said actuating button 17.

Figure 9:
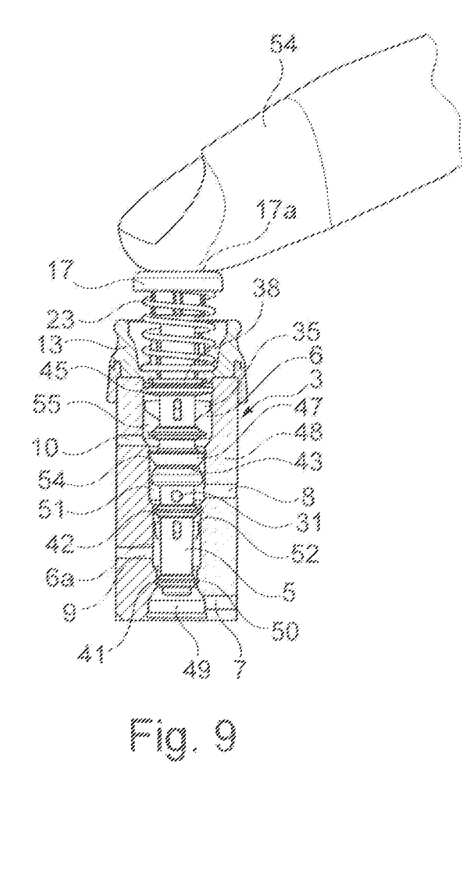
FIG. 9 shows a longitudinal section of the valve unit, said valve unit being covered on the end side by way of a finger, with the result that an outlet of the gaseous medium via an actuating button is prevented and, as a consequence, said gaseous medium flows into the endoscope.
Figure 10:
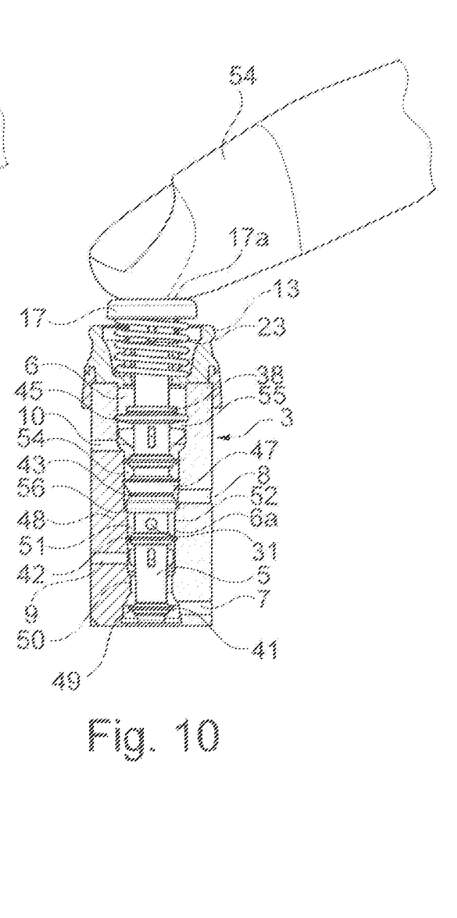
FIG. 10 shows a longitudinal section of the valve unit, the valve slide being displaced in the longitudinal direction in such a way that the purging liquid is fed from a purging liquid inflow channel via the valve slide to a purging liquid outlet channel and therefore to the endoscope.

A smooth-walled configuration of the outer circumferential face 40 and an integrally joined connection of the sealing rings 41, 42, 43, 44 and 45 to said outer circumferential face 40 are essential. Here, the sealing ring 43 has a distal part region 46, in which it acts as a seat sealing ring, as the following FIG. 10 shows, in particular. A proximal part region 47 of the sealing ring 43 is configured as a grooved ring and acts, as the following FIGS. 9 and 10 show, as a check valve for the air which flows through the valve unit 3. The remaining sealing rings 41, 42, 44 and 45 in each case have at least one radial sealing lip.

Figure 4:
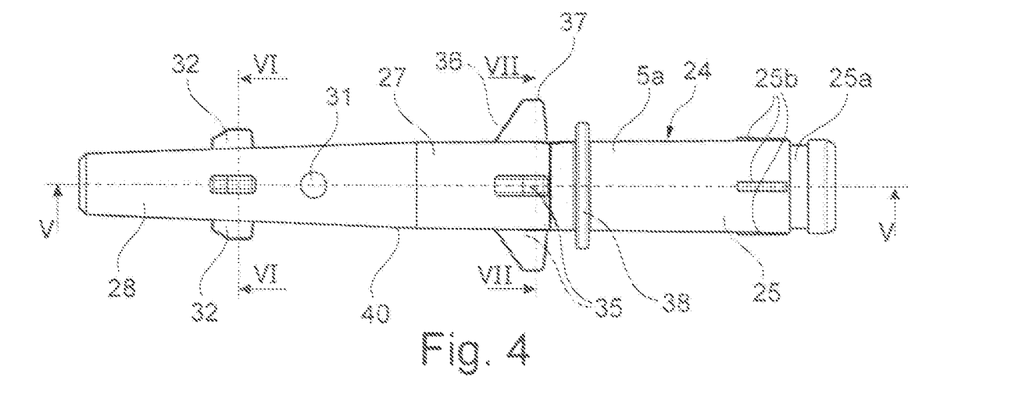
FIG. 4 shows a side view of a hollow body which is provided for the production of the valve slide.
Figure 5:
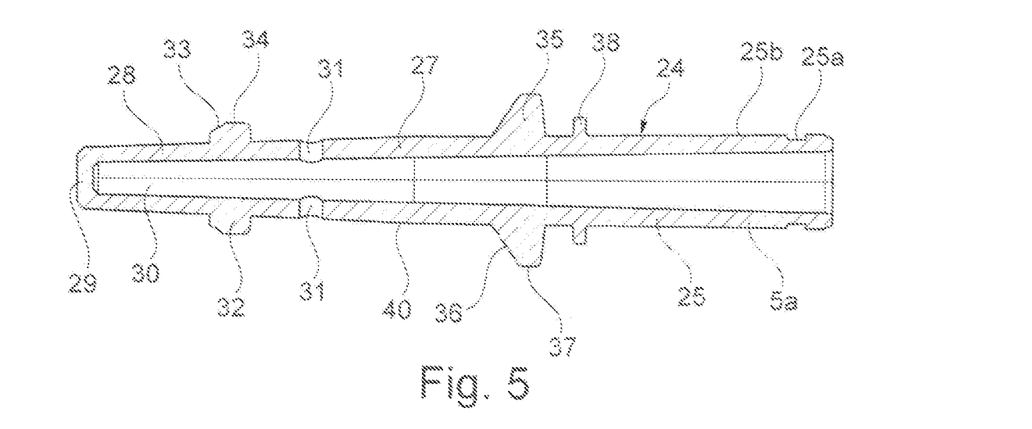
FIG. 5 shows a longitudinal section according to line V-V through the hollow body in FIG. 4.

FIGS. 4, 5, 6 and 7 show the prism-like hollow body 24 and sectional illustrations of the latter. The hollow body 24 is shown in FIGS. 4 and 5 in a state before the sealing rings 41, 42, 43, 44 and 45 are connected to its outer circumferential face 40 in an integrally joined manner. Initially, FIG. 4 shows a side view of the prism-like hollow body 24 with the first runners 32, the second runners 35 and the annular projection 38.

Figure 6:
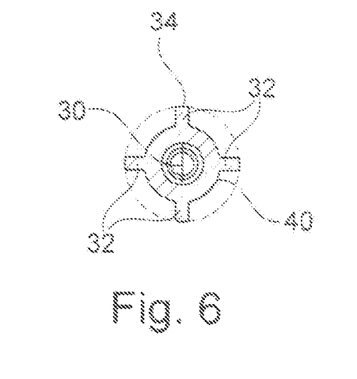
FIG. 6 shows a cross section according to line VI-VI through the hollow body in FIG. 4.
Figure 7:
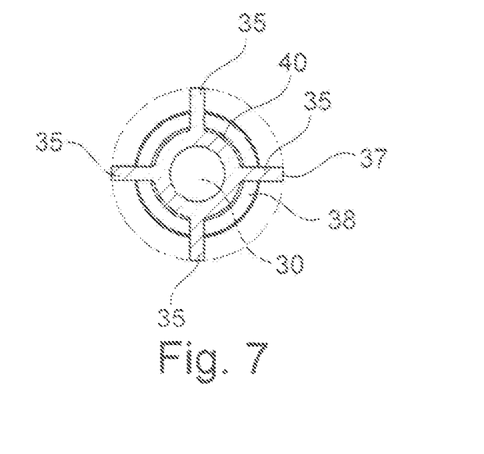
FIG. 7 shows a cross section according to line VII-VII through the hollow body in FIG. 4.

It can be gathered from the illustration that the outer circumferential face 40 of the hollow body 24 runs differently in the three different part regions of the longitudinal extent. In the first part region, in which the hollow body 24 (as FIG. 5 shows) is formed by way of the first outer wall 25, said hollow body 24 is of substantially cylindrical design. In the second and third part region of the hollow body 24, in which said hollow body 24 has the outer walls 27 and 28, the latter in contrast run in a frustoconical manner with a different inclination. FIGS. 6 and 7 illustrate the configuration of the runners 32 and 35 in corresponding cross sections through the hollow body 24.

Figure 8:
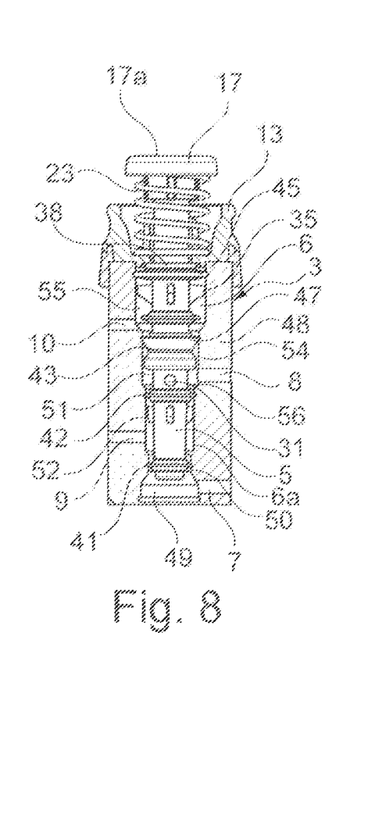
FIG. 8 shows the valve unit which is shown in longitudinal section in a first switching state, in which neither a gaseous medium nor a purging liquid is fed to a distal end of the endoscope.

In the further FIGS. 8 to 10, in contrast to the embodiment according to FIG. 1, the valve unit 3 is provided with a valve housing 48, with the result that the entire valve unit can be inserted into the correspondingly designed manual actuation part 1. The receiving bore 6 which receives the longitudinally displaceable valve slide 5 runs in the valve housing 48. The receiving bore 6 is overall of step-like configuration and is widened radially at its distal end in order to form an inflow space 49 which is connected to the purging liquid inflow channel 8. This is adjoined by a sealing region 50 which is configured on an inner circumferential face 6a of the receiving bore 6 and with which the sealing ring 41 can interact, depending on the position of the valve slide 5.

A control space 51 is configured between the sealing rings 42 and 43, it being possible, as has already been shown in conjunction with FIG. 3, for the sealing ring 43 to assume the function of a check valve. Here, that part region 47 of the sealing ring 43 which is configured as a grooved ring interacts with a sealing region 52 which is formed on the inner circumferential face 6a, whereas the part region which is configured as a seat sealing ring fulfills its sealing function together with a valve seat 56 which is provided at the end of the sealing region 52. A sealing region 55 which is produced by way of a further radial widened portion of the receiving bore 6 is situated above the abovementioned sealing region 52, in which sealing region 55 the runners 35 are guided, and with which sealing region 55 the sealing ring 45 interacts in order to seal the valve housing 48 in the proximal direction.

In FIG. 8, the valve unit 3 is situated first of all in its non-actuated state, in which the annular projection 38 bears against the retaining ring 21 under the prestress of the compression spring 23. In said position of the valve slide 5, the air which enters under pressure into the control space 51 from the air inlet channel 8 passes out of said control space 51 via the transverse bore 31 into the longitudinal channel (longitudinal channel in FIG. 3). Therefore, the air which is fed to the valve unit 3 exits in a pressureless manner from the proximal end of the valve slide 5, namely in the middle of the actuating button 17. Here, the sealing ring 41 bears sealingly in the sealing region 50 of the receiving bore 6, with the result that the purging liquid outlet channel 9 is shut off with respect to the purging liquid inflow channel 7. Therefore, neither compressed air for an insufflation nor purging liquid for a purging operation passes to the distal end of the endoscope 2.

If, as shown in FIG. 9, a fingertip of a finger 54 is then placed by the person operating the endoscope onto the end side 17a of the actuating button 17, this leads to it no longer being possible for the compressed air to exit via the above-described longitudinal channel 30. This achieves a situation where a pressure is built up in the control space 51, which pressure brings it about that that part region 47 of the sealing ring 43 which is configured as a grooved ring lifts up from a sealing region 54 which interacts with it. Therefore, the compressed air can be fed to the distal end of the endoscope 2 via the air outlet channel 10.

According to FIG. 10, the finger 52 is placed not only onto the end side of the actuating button 17, but a force is also additionally exerted on the valve slide 5 in the longitudinal direction, which force leads to the longitudinal displacement of said valve slide 5 counter to the force of the compression spring 23. In an end position of the valve slide 5, the sealing ring 41 passes into the inflow space 49 and does not assume a sealing function, with the result that purging liquid passes from the purging liquid inflow channel 7 into the purging liquid outlet channel 9. Here, the control space 51 is sealed by means of the sealing ring 42. Moreover, that distal part region 46 of the sealing ring 43 which is configured as a seat sealing ring bears against the valve seat 56. This prevents the compressed air from continuing to be conducted via the transverse bore 31 and the longitudinal channel 30 as far as the end side 17a of the actuating button 17.

Figure 11:
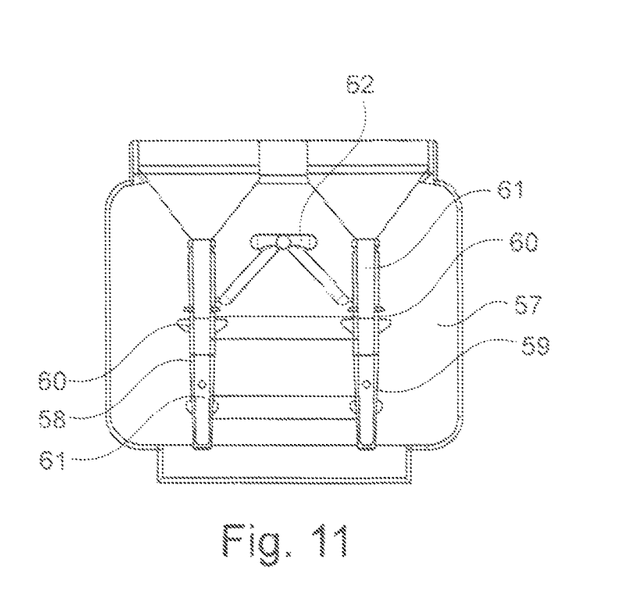
FIG. 11 shows a plan view of a lower half of an injection mold for producing the hollow body.

Finally, FIG. 11 shows one half of a first injection mold 57, by means of which the prism-like hollow body according to FIGS. 4 and 5 is produced. The overall injection mold 57 is formed by way of two halves. The present injection mold 57 has two cavities 58 and 59, with the result that two prism-like hollow pistons 24 can be produced from an acrylonitrile butadiene styrene (ABS) in one molding operation. Each of said cavities 58 and 59 has a mold 60 and a core 61. The liquid plastic is fed to the cavities 58 and 59 via a gating system 62. After the solidification of the blanks, that is to say of the two hollow bodies 24 and 24a, the injection mold 57 is opened, and the two hollow bodies 24, 24a are ejected from an ejector side of the injection mold 57 by means of an ejector (not shown in greater detail).

Figure 12:
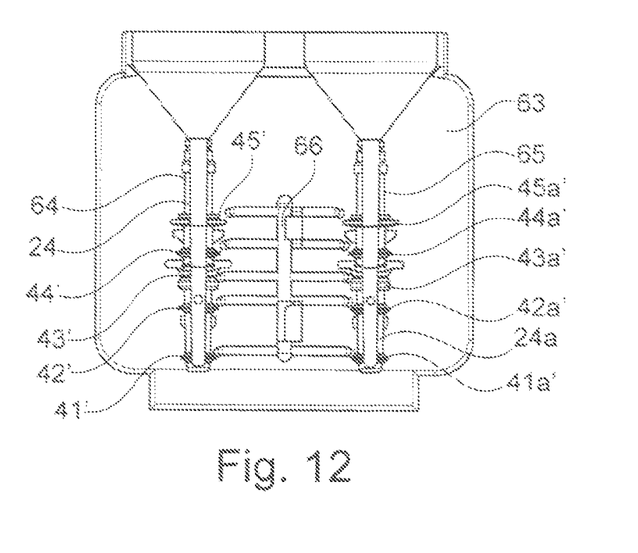
FIG. 12 shows a plan view of a lower half of an injection mold with a hollow body which is arranged therein, sealing rings being molded onto the hollow body in said injection mold.

One half of a second injection mold 63 with two molds 64 and 65 is apparent from FIG. 12, into which the two hollow bodies 24 and 24a which are produced in the first injection mold 57 are inserted. The molds 54 and 65 have a negative contour 41', 42', 43', 44' and 45', and 41a', 42a', 43a', 44a' and 45a' of the respective sealing rings 41, 42, 43, 44 and 45 which are shown in FIGS. 2 and 3. The two hollow bodies 24 and 24a have a residual temperature of from 60 to 100° C. when the thermoplastic elastomer (TE) is injected into the molds via a gating system 66. Subsequently, demolding of the two substantially finished valve slides takes place, which valve slides are subsequently provided merely with the compression spring 23, the retaining ring 13 and the actuating button 17.

LIST OF DESIGNATIONS

1 Manual actuation part of 2
2 Endoscope
3 Valve unit
4 Drain valve
5 Valve slide
5a Proximal end of 5
6 Receiving bore
6a Inner circumferential face of 6
7 Purging liquid inflow channel
8 Air inlet channel
9 Purging liquid outlet channel
10 Air outlet channel
11 Compressed air source
11a Compressed air line
12 Purging liquid storage vessel
13 Retaining ring
14 Elastic sleeve
15 Housing of 1
16 Collar of 15
17 Actuating button
17a Trough-like end side of 17
18 Drain channel
19 Collecting channel
20 Collecting reservoir
21 Retaining ring
22 Pushbutton
22a Compression spring of 4
23 Compression spring of 3
24 Prism-like hollow body
24a Prism-like hollow body
25 First section of the outer wall
25a End-side groove in 25
25b Ribs of 25
26 Longitudinal slots in 22
27 Second section of the outer wall
28 Third section of the outer wall
29 End-side wall
30 Longitudinal channel
31 Transverse bore
32 First runners
33 Bevel of 32
34 End of 32
35 Second runners
36 Bevel of 35
37 End of 35
38 Annular projection
39 Hub of 13
40 Outer circumferential face of 24
41 Sealing ring
41a Mold for sealing ring
41a' Mold for sealing ring
42 Sealing ring
42a Mold for sealing ring
42a' Mold for sealing ring
43 Sealing ring
43a Mold for sealing ring
43a' Mold for sealing ring
44 Sealing ring
44a Mold for sealing ring
44a' Mold for sealing ring
45 Sealing ring
45a Mold for sealing ring
45a' Mold for sealing ring
46 Distal part region of 43 which is configured as a seat sealing ring
47 Proximal part region of 43 which is configured as a grooved ring
48 Valve housing of 3
49 Inflow space
50 Sealing region
51 Control space
52 Sealing region
53 Radial widened portion
54 Sealing region
55 Sealing region
56 Valve seat
57 First injection mold
58 Cavity of 57
59 Cavity of 57
60 Mold
61 Core
62 Gating system
63 Second injection mold
64 Mold of 63
65 Mold of 63
66 Gating system

The invention claimed is:

1. A valve slide for a valve unit configured as an insufflation and purging valve, of a medical endoscope, which valve slide is configured to be insertable into a receiving bore which is configured at least indirectly in a manual actuation part of the endoscope and is connected to air inlet channels and air outlet channels and to purging liquid inflow channels and purging liquid outlet channels, the valve slide comprising:
 a distal control section by which the valve slide is insertable into the receiving bore;
 a proximal actuating section that extends through a retaining ring and is provided with an actuating button, the actuating button being supported on the retaining ring via a compression spring;
 an annular projection arranged to support the actuating button and to interact as a stop that acts in an axial direction with the retaining ring; and
 sealing rings provided on the distal control section so as to project radially and are provided to seal at least one control space of the valve unit in a manner which slides on an inner circumferential face of the receiving bore,
 wherein the distal control section has an outer circumferential face and radial guide sections provided on the outer circumferential face, wherein the outer circumferential face is of smooth-walled configuration apart from the projection and the radial guide sections, and
 wherein the sealing rings are connected in an integrally joined manner to the smooth-walled outer circumferential face
 wherein the valve slide is configured as a prism-shaped hollow body with a circularly annular cross section, in which a longitudinal channel is provided for conducting the compressed air, and
 wherein the proximal actuating section has proximal ribs and an end-side groove, the prism-shaped hollow body is configured with a substantially identical wall thickness apart from where the regions of the radial guide sections, the annular projection, the proximal ribs and the end-side groove are located.

2. The valve slide according to claim 1, wherein the hollow body is acrylonitrile butadiene styrene, and the sealing rings are a thermoplastic elastomer.

3. The valve slide according to claim 1, wherein the hollow body is of frustoconical configuration at least in the distal control section.

4. The valve slide according to claim 1, wherein the guide sections are configured as runners which are distributed uniformly on the circumference of the hollow body and are formed by way of attachments which extend radially from the circumference.

5. The valve slide according to claim 1, wherein at least one transverse bore which communicates with the longitudinal channel is provided in a wall of the hollow body in a region which lies between two sealing rings.

* * * * *